(12) United States Patent
Fischer et al.

(10) Patent No.: US 8,211,931 B2
(45) Date of Patent: Jul. 3, 2012

(54) ACTIVE COMPOUND COMBINATIONS HAVING INSECTICIDAL AND ACARICIDAL PROPERTIES

(75) Inventors: Reiner Fischer, Monheim (DE); Heike Hungenberg, Langenfeld (DE); Ralf Nauen, Langenfeld (DE); Hans-Jürgen Schnorbach, Monheim (DE); Wolfgang Thielert, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 614 days.

(21) Appl. No.: 12/304,904

(22) PCT Filed: Jun. 5, 2007

(86) PCT No.: PCT/EP2007/004963
§ 371 (c)(1),
(2), (4) Date: May 21, 2009

(87) PCT Pub. No.: WO2007/144086
PCT Pub. Date: Dec. 21, 2007

(65) Prior Publication Data
US 2010/0048661 A1 Feb. 25, 2010

(30) Foreign Application Priority Data
Jun. 16, 2006 (DE) .................. 10 2006 027 731

(51) Int. Cl.
A01N 63/00 (2006.01)
A01N 43/36 (2006.01)
A01N 43/38 (2006.01)
A01P 3/00 (2006.01)
A01P 7/00 (2006.01)

(52) U.S. Cl. ........................ 514/409; 514/423

(58) Field of Classification Search ................ 514/409, 514/423
See application file for complete search history.

(56) References Cited

U.S. PATENT DOCUMENTS

| | | | |
|---|---|---|---|
| 4,985,063 A | 1/1991 | Fischer et al. | |
| 5,045,560 A | 9/1991 | Fischer et al. | |
| 5,116,836 A | 5/1992 | Fischer et al. | |
| 5,225,434 A | 7/1993 | Bertram et al. | |
| 5,258,527 A | 11/1993 | Krauskopf et al. | |
| 5,262,383 A | 11/1993 | Fischer et al. | |
| 5,462,913 A | 10/1995 | Fischer et al. | |
| 5,504,057 A | 4/1996 | Fischer et al. | |
| 5,589,469 A | 12/1996 | Fischer et al. | |
| 5,622,917 A | 4/1997 | Fischer et al. | |
| 5,683,965 A | 11/1997 | Bachmann et al. | |
| 5,811,374 A | 9/1998 | Bertram et al. | |
| 5,830,826 A | 11/1998 | Fischer et al. | |
| 6,110,872 A | 8/2000 | Lieb et al. | |
| 6,114,374 A | 9/2000 | Lieb et al. | |
| 6,133,296 A | 10/2000 | Lieb et al. | |
| 6,140,358 A | 10/2000 | Lieb et al. | |
| 6,200,932 B1 | 3/2001 | Fischer et al. | |
| 6,251,830 B1 | 6/2001 | Fischer et al. | |
| 6,288,102 B1 | 9/2001 | Hagemann et al. | |
| 6,316,486 B1 | 11/2001 | Lieb et al. | |
| 6,358,887 B1 | 3/2002 | Fischer et al. | |
| 6,380,246 B1 | 4/2002 | Lieb et al. | |
| 6,417,370 B1 | 7/2002 | Lieb et al. | |
| 6,451,843 B1 | 9/2002 | Lieb et al. | |
| 6,458,965 B1 | 10/2002 | Lieb et al. | |
| 6,472,419 B1 | 10/2002 | Fischer et al. | |
| 6,511,942 B1 | 1/2003 | Lieb et al. | |
| 6,589,976 B1 | 7/2003 | Fischer et al. | |
| 6,608,211 B1 | 8/2003 | Hagemann et al. | |
| 6,642,180 B1 | 11/2003 | Fischer et al. | |
| 6,861,391 B1 | 3/2005 | Fischer et al. | |
| 6,894,005 B1 | 5/2005 | Maetzke et al. | |
| 7,795,303 B2 | 9/2010 | Fischer et al. | |
| 8,013,172 B2 | 9/2011 | Fischer et al. | |
| 2003/0216260 A1 | 11/2003 | Ruther et al. | |
| 2005/0054535 A1 | 3/2005 | Fischer et al. | |
| 2006/0160847 A1 | 7/2006 | Fischer et al. | |
| 2006/0166829 A1 | 7/2006 | Fischer et al. | |
| 2007/0015664 A1 | 1/2007 | Fischer et al. | |
| 2007/0032539 A1 | 2/2007 | Himmler | |
| 2007/0129252 A1 | 6/2007 | Fischer et al. | |
| 2007/0225167 A1 | 9/2007 | Fischer et al. | |
| 2007/0225170 A1 | 9/2007 | Fischer et al. | |
| 2007/0244007 A1 | 10/2007 | Fischer et al. | |
| 2007/0265266 A1 | 11/2007 | Fischer et al. | |
| 2007/0270416 A1 | 11/2007 | Funke et al. | |
| 2007/0275858 A1 | 11/2007 | Fischer et al. | |
| 2007/0276023 A1 | 11/2007 | Fischer et al. | |
| 2007/0298968 A1 | 12/2007 | Bretschneider et al. | |
| 2007/0298969 A1 | 12/2007 | Fischer et al. | |
| 2008/0167188 A1 | 7/2008 | Fischer et al. | |
| 2008/0220973 A1 | 9/2008 | Fischer et al. | |

(Continued)

FOREIGN PATENT DOCUMENTS

DE 102 31 333 A1 1/2004
(Continued)

OTHER PUBLICATIONS

Elbert, A., et al., "Field Development of Oberon® for whitefly and mite control in vegetables, cotton, corn, strawberries, ornamentals and tea," Pflanzenschutz-Nachrichten Bayer 58:441-468, Bayer CropScience (2005).

Hardman, J.M., et al., "An index for selective toxicity of miticides to phytophagous mites and their predators based on orchard trials," Pest. Manag. Sci. 59:1321-1332, John Wiley & Sons, Ltd. (2003).

Izquierdo, J., et al., "Development of Envidor® for the control of spider mites in Spanish citrus production," Pflanzenschutz-Nachrichten Bayer 55:255-266, Bayer CropScience (2002).

Jhansi Lakshmi, V., et al., "Relative safety of selected acaricides to three hemipteran natural enemies of planthoppers in rice ecosystem," J. Biol. Control 20:141-146, Society for Biocontrol Advancement, Bangalore, India (2006).

De Maeyer, L., et al., "Envidor®—a new acaricide for IPM in pomefruit orchards," Pflanzenschutz-Nachrichten Bayer 55:211-236, Bayer CropScience, (2002).

(Continued)

Primary Examiner — John Pak
(74) Attorney, Agent, or Firm — Sterne, Kessler, Goldstein & Fox P.L.L.C.

(57) ABSTRACT

The novel active compound combinations consisting, firstly, of cyclic ketoenols and, secondly, of beneficial species (natural enemies) have very good insecticidal and/or acaricidal properties.

7 Claims, No Drawings

U.S. PATENT DOCUMENTS

| | | | |
|---|---|---|---|
| 2008/0287435 A1 | 11/2008 | Fischer et al. |
| 2008/0305955 A1 | 12/2008 | Bretschneider et al. |
| 2008/0318776 A1 | 12/2008 | Fischer et al. |
| 2009/0012100 A1 | 1/2009 | Fischer et al. |
| 2009/0012152 A1 | 1/2009 | Fischer et al. |
| 2009/0029858 A1 | 1/2009 | Fischer et al. |
| 2009/0215624 A1 | 8/2009 | Fischer et al. |
| 2009/0298828 A1 | 12/2009 | Fischer et al. |
| 2010/0056620 A1 | 3/2010 | Fischer et al. |
| 2010/0173987 A1 | 7/2010 | Fischer et al. |

FOREIGN PATENT DOCUMENTS

| | | |
|---|---|---|
| DE | 10 2005 051 325 A | 5/2007 |
| EP | 0 355 599 A1 | 2/1990 |
| EP | 0 377 893 A2 | 7/1990 |
| EP | 0 415 211 A2 | 3/1991 |
| EP | 0 442 073 A2 | 8/1991 |
| EP | 0 442 077 A2 | 8/1991 |
| EP | 0 456 063 A2 | 11/1991 |
| EP | 0 521 334 A1 | 1/1993 |
| EP | 0 596 298 A2 | 5/1994 |
| EP | 0 613 884 A2 | 9/1994 |
| EP | 0 668 267 A1 | 8/1995 |
| WO | WO 95/01971 A1 | 1/1995 |
| WO | WO 95/20572 A1 | 8/1995 |
| WO | WO 95/26954 A1 | 10/1995 |
| WO | WO 96/25395 A1 | 8/1996 |
| WO | WO 96/35664 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 98/05638 A2 | 2/1998 |
| WO | WO 98/06721 A1 | 2/1998 |
| WO | WO 98/25928 A1 | 6/1998 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 01/09092 A1 | 2/2001 |
| WO | WO 01/17972 A2 | 3/2001 |
| WO | WO 01/23354 A2 | 4/2001 |
| WO | WO 01/74770 A1 | 10/2001 |
| WO | WO 03/013249 A1 | 2/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/111042 A1 | 12/2004 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |
| WO | WO 2005/066125 A1 | 7/2005 |
| WO | WO 2005/092897 A2 | 10/2005 |
| WO | WO 2006/000355 A1 | 1/2006 |
| WO | WO 2006/029799 A1 | 3/2006 |
| WO | WO 2006/056281 A1 | 6/2006 |
| WO | WO 2006/056282 A1 | 6/2006 |
| WO | WO 2006/089633 A2 | 8/2006 |

OTHER PUBLICATIONS

International Search Report for International Application No. PCT/EP2007/004963, European Patent Office, Netherlands, mailed on Nov. 7, 2007, Search completed Oct. 26, 2007.

Colby, S. R., "Calculating Synergistic and Antagonistic Responses of Herbicide Combinations," *Weeds* 15:20-22, Weed Science Society of America (1966).

Co-pending U.S. Appl. No. 12/303,206, Fischer, R., et al., filed May 23, 2007.

Bauer, T.A., et al., "Response of Selected Weed Species to Postemergence Imazethapyr and Bentazon," *Weed Tech.* 9:236-242, The Weed Science Society of America (1995).

Blackshaw, R.E., "HOE-39866 Use in Chemical Fallow Systems,"*Weed Tech.* 3: 420-428, The Weed Science Society of America (1989).

Blackshaw, R.E., "Synergistic Mixes of DPX-A7881 and Clopyralid in Canola (*Brassica napus*)," *Weed Tech.* 3:690-695, The Weed Science Society of America (1989).

Blackshaw, R.E., et al., "Herbicide Combinations for Postemergent Weed Control in Safflower (*Carthamus tinctorius*),"*Weed Tech.* 4:97-104, The Weed Science Society of America (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America (2004).

Bradley, P.R., et al., "Response of Sorghum (Sorghum bicolor) to Atrazine, Ammonium Sulfate, and Glyphosate," *Weed Tech.* 14:15-18, The Weed Science Society of America (2000).

Buker, III, R.S., et al., "Confirmation and Control of Paraquat-Tolerant Goosegrass (*Eleusine indica*) Biotype," *Weed Tech.* 16:309-313, The Weed Science Society of American (2002).

Burke, I.C., et al., "CGA-362622 Antagonizes Annual Grass Control with Clethodim," *Weed Tech.* 16:749-754, The Weed Science Society of America (2002).

Flint, J.L., et al., "Analyzing Herbicide Interactions, A Statistical Treatment of Society of Colby's Method," *Weed Tech.* 2:304-309, The Weed Society of America (1988)

Gillespie, G.R., and Nalewaja, J.D., "Wheat (*Triticum aestivum*) Response to Triallate Plus Chlorsulfuron," *Weed Tech* 3:20-23, The Weed Science Society of America (1989).

Green, J.M., et al., "Metribuzin and Chlorimuron Mixtures for Preemergence Broadleaf Weed Control in Soybeans, Glycine max," *Weed Tech.* 2:355-363, The Weed Science Society of America (1988).

Harker, K.N., and O'Sullivan, P.A., "Synergistic Mixtures of Sethoxydim and Fluazifop on Annual Grass Weed," *Weed Tech.* 5:310-316, The Weed Science Society of America (1991).

Kent, L.M., et al., "Effect of Amonium Sulfate, Imazapyr, and Environment on the Phytotxicity of Imazethapyr," *Weed Tech.* 5:202-205, The Weed Science of America (1991).

Kotoula-Syka, E., et al., "Interaction between SAN 582H and Selected Safeners on Gran Sorghum (Sorghum bicolor) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Oryza sativa*)," *Weed Tech.* 16:659-663, The Weed Science of Society of America (2002).

Norris, J.L., et al., "Weed Control from Hebicide Combinations with Three Formulations of Glyphosate," *Weed Tech.* 15:552-558, The Weed Science Society of American (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (Glycine max) with CGA-277476 and Four Postmergence Herbicieds," *Weed Tech.* 14:617-623, The Weed Science Society of America (2000).

Rummens, F.H.A., "An Improved Definition of Synetgistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J Econ. Entomol.* 53:887-892, United States (1960).

Tammes, P.M.L., "Isoboles, A Graphic Representation of Synergism in Pesticides," *Neth. J. Plant Path. 70*:73-80, Springer, Germany (1964).

Wehtje, G. And Walker, R.H., "Interaction of Glyphosate and 2,4-DB for the Control of Selected Morningglory (*Ipomoea* spp.) Species," *Weed Tech. 11*:152-156, The Weed Science Society of America (1997).

Zhang, W., et al., "Fenoxaprop Interactions for Barnyardgrass (*Echinochloa crusgalli*) Control in Rice," *Weed Tech. 19*:293-297, The Weed Science Society of America (2005).

ACTIVE COMPOUND COMBINATIONS HAVING INSECTICIDAL AND ACARICIDAL PROPERTIES

This application is a National Stage of International Application No. PCT/EP2007/004963, filed Jun. 5, 2007, which claims the benefit of German Patent Application No. 10 2006 027 731.7, filed Jun. 16, 2006.

The present invention relates to novel active compound combinations consisting, firstly, of known cyclic ketoenols and, secondly, of beneficial species (natural enemies), which combinations are highly suitable for controlling animal pests such as insects and/or unwanted acarids.

It is already known that certain cyclic ketoenols have herbicidal, insecticidal and acaricidal properties. The activity of these substances is good; however, at low application rates it is sometimes unsatisfactory.

Known to have herbicidal, insecticidal or acaricidal action are unsubstituted bicyclic 3-arylpyrrolidine-2,4-dione derivatives (EP-A-355 599 and EP-A-415 211), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073), and also tetramic acid derivatives, from EP-A-456 063, EP-A-521 334, EP-A-596 298, EP-A-613 884, WO 95/01997, WO 95/26954, WO 95/20572, EP-A-0 668267, WO 96/25395, WO 96/35664, WO 97/01535, WO 97/02243, WO 97/36868, WO 97/43275, WO 98/05638, WO 98/06721, WO 98/25928, WO 99/16748, WO 99/24437, WO 99/43649, WO 99/48869, WO 99/55673, WO 01/09092, WO 91/17972, WO 01/23354, WO 01/74770, WO 03/013249, WO 2004/007448, WO 2004/024688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633 and DE-A-05 05 1325.

It is furthermore already known that numerous beneficial species are used for controlling insects and spider mites: "Knowing and recognizing"; M. H. Malais, W. J. Ravensberg, published by Koppert B. V., Reed Business Information (2003). However, the use of beneficial species on their own is not always satisfactory.

It has now been found that compounds of the formula (I)

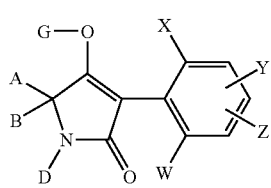

(I)

in which
X represents halogen, alkyl, alkoxy, haloalkyl, haloalkoxy or cyano,
W, Y and Z independently of one another represent hydrogen, halogen, alkyl, alkoxy, haloalkyl, haloalkoxy or cyano,
A represents hydrogen, in each case optionally halogen-substituted alkyl, alkoxyalkyl, saturated, optionally substituted cycloalkyl in which optionally at least one ring atom is replaced by a heteroatom,
B represents hydrogen or alkyl,
A and B together with the carbon atom to which they are attached represent a saturated or unsaturated unsubstituted or substituted cycle which optionally contains at least one heteroatom,
D represents hydrogen or an optionally substituted radical from the group consisting of alkyl, alkenyl, alkoxyalkyl, saturated cycloalkyl in which optionally one or more ring members are replaced by heteroatoms,
A and D together with the atoms to which they are attached represent a saturated or unsaturated cycle which optionally contains at least one heteroatom and is unsubstituted or substituted in the A,D moiety,
G represents hydrogen (a) or represents one of the groups

(b)

(c)

(d)

(e)

(f)

E or

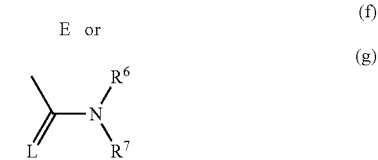

(g)

in which
E represents a metal ion or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$ represents optionally halogen-substituted alkyl or optionally substituted phenyl,
$R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and
$R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the nitrogen atom to which they are attached represent an optionally substituted ring which is optionally interrupted by oxygen or sulphur, in combination with beneficial species from the orders or sub-orders of the Araneae, Acari, Hymenoptera, Coleoptera, Neuroptera, Tysanoptera, Heteroptera, Diptera, Hemiptera, Dermaptera and/or Parasitiformes have very good insecticidal and/or acaricidal properties.

Surprisingly, the insecticidal and/or acaricidal activity of the active compound/beneficial species combinations according to the invention is better than the activities of the individual active compound and the beneficial species alone. An unforeseeable enhancement of activity is present.

Furthermore, it has been found that, using the active compound/beneficial species combinations according to the invention, applications of toxicologically and/or ecologically less favourable active compounds may be substituted achieving a comparable activity, which is beneficial especially with respect to safety of the user and/or the environment. Moreover, it has been found that spray applications may be reduced.

In addition to at least one active compound of the formula (I), the active compound/beneficial species combinations according to the invention comprise at least one beneficial species from the orders or sub-orders mentioned above.

Preference is given to using active compound/beneficial species combinations comprising compounds of the formula (I) in which the radicals are as defined below:

W preferably represents hydrogen, $C_1$-$C_4$-alkyl, $C_1$-$C_4$-alkoxy, chlorine, bromine or fluorine, X preferably represents $C_1$-$C_4$-alkyl, $C_1$-$C_4$-alkoxy, $C_1$-$C_4$-haloalkyl, fluorine, chlorine or bromine, Y and Z independently of one another preferably represent hydrogen, $C_1$-$C_4$-alkyl, halogen, $C_1$-$C_4$-alkoxy or $C_1$-$C_4$-haloalkyl, A preferably represents hydrogen or in each case optionally halogen-substituted $C_1$-$C_6$-alkyl or $C_3$-$C_8$-cycloalkyl, B preferably represents hydrogen, methyl or ethyl, A, B and the carbon atom to which they are attached preferably represent saturated $C_3$-$C_6$-cycloalkyl in which optionally one ring member is replaced by oxygen or sulphur and which is optionally mono- or disubstituted by $C_1$-$C_4$-alkyl, trifluoromethyl or $C_1$-$C_4$-alkoxy, D preferably represents hydrogen, in each case optionally fluorine- or chlorine-substituted $C_1$-$C_6$-alkyl, $C_3$-$C_4$-alkenyl or $C_3$-$C_6$-cycloalkyl, A and D together preferably represent in each case optionally methyl-substituted $C_3$-$C_4$-alkanediyl in which optionally one methylene group is replaced by sulphur, G preferably represents hydrogen (a) or represents one of the groups

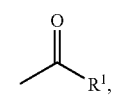
(b)

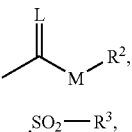
(c)

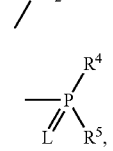
(d)

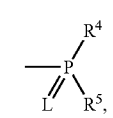
(e)

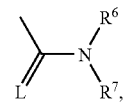
(f)

(g)

in particular (a), (b), (c) or (g),
in which
E represents a metal ion or an ammonium ion,
L represents oxygen or sulphur and
M represents oxygen or sulphur, $R^1$ preferably represents in each case optionally halogen-substituted $C_1$-$C_{10}$-alkyl, $C_2$-$C_{10}$-alkenyl, $C_1$-$C_4$-alkoxy-$C_1$-$C_4$-alkyl, $C_1$-$C_4$-alkylthio-$C_1$-$C_4$-alkyl or optionally fluorine-, chlorine-, $C_1$-$C_4$-alkyl- or $C_1$-$C_2$-alkoxy-substituted $C_3$-$C_6$-cycloalkyl,
represents optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl,
represents in each case optionally chlorine- or methyl-substituted pyridyl or thienyl, $R^2$ preferably represents in each case optionally fluorine- or chlorine-substituted $C_1$-$C_{10}$-alkyl, $C_2$-$C_{10}$-alkenyl, $C_1$-$C_4$-alkoxy-$C_2$-$C_4$-alkyl,
represents optionally methyl- or methoxy-substituted $C_5$-$C_6$-cycloalkyl or
represents in each case optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl or benzyl, $R^3$ preferably represents optionally fluorine-substituted $C_1$-$C_4$-alkyl or represents optionally fluorine-, chlorine-, bromine-, $C_1$-$C_4$-alkyl-, $C_1$-$C_4$-alkoxy-, trifluoromethyl-, trifluoromethoxy-, cyano- or nitro-substituted phenyl, $R^4$ preferably represents in each case optionally fluorine- or chlorine-substituted $C_1$-$C_4$-alkyl, $C_1$-$C_4$-alkoxy, $C_1$-$C_4$-alkylamino, $C_1$-$C_4$-alkylthio or represents in each case optionally fluorine-, chlorine-, bromine-, nitro-, cyano-, $C_1$-$C_4$-alkoxy-, trifluoromethoxy-, $C_1$-$C_4$-alkylthio-, $C_1$-$C_4$-haloalkylthio-, $C_1$-$C_4$-alkyl- or trifluoromethyl-substituted phenyl, phenoxy or phenylthio, $R^5$ preferably represents $C_1$-$C_4$-alkoxy or $C_1$-$C_4$-thioalkyl, $R^6$ preferably represents $C_1$-$C_6$-alkyl, $C_3$-$C_6$-cycloalkyl, $C_1$-$C_6$-alkoxy, $C_3$-$C_6$-alkenyl, $C_1$-$C_4$-alkoxy-$C_1$-$C_4$-alkyl, $R^7$ preferably represents $C_1$-$C_6$-alkyl, $C_3$-$C_6$-alkenyl or $C_1$-$C_4$-alkoxy-$C_1$-$C_4$-alkyl, $R^6$ and $R^7$ together preferably represent an optionally methyl- or ethyl-substituted $C_3$-$C_6$-alkylene radical in which optionally one carbon atom is replaced by oxygen or sulphur.

Particular preference is given to using active compound/beneficial species combinations comprising compounds of the formula (I) mentioned above in which the radicals are as defined below:

W particularly preferably represents hydrogen, methyl, ethyl, chlorine, bromine or methoxy, X particularly preferably represents chlorine, bromine, methyl, ethyl, propyl, isopropyl, methoxy, ethoxy or trifluoromethyl, Y and Z independently of one another particularly preferably represent hydrogen, fluorine, chlorine, bromine, methyl, ethyl, propyl, isopropyl, trifluoromethyl or methoxy, A particularly preferably represents methyl, ethyl, propyl, isopropyl, butyl, isobutyl, sec-butyl, tert-butyl, cyclopropyl, cyclopentyl or cyclohexyl, B particularly preferably represents hydrogen, methyl or ethyl, A, B and the carbon atom to which they are attached particularly preferably represent saturated $C_6$-cycloalkyl in which optionally one ring member is replaced by oxygen and which is optionally monosubstituted by methyl, ethyl, methoxy, ethoxy, propoxy or butoxy, D particularly preferably represents hydrogen, represents methyl, ethyl, propyl, isopropyl, butyl, isobutyl, allyl, cyclopropyl, cyclopentyl or cyclohexyl, A and D together particularly preferably represent optionally methyl-substituted $C_3$-$C_4$-alkanediyl, G particularly preferably represents hydrogen (a) or represents one of the groups

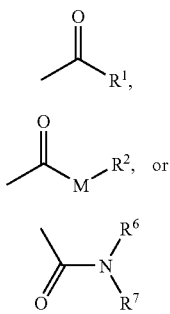

in which

M represents oxygen or sulphur, $R^1$ particularly preferably represents $C_1$-$C_8$-alkyl, $C_2$-$C_4$-alkenyl, methoxymethyl, ethoxymethyl, ethylthiomethyl, cyclopropyl, cyclopentyl or cyclohexyl, represents optionally fluorine-, chlorine-, bromine-, cyano-, nitro-, methyl-, ethyl-, methoxy-, trifluoromethyl- or trifluoromethoxy-substituted phenyl, represents in each case optionally chlorine- or methyl-substituted pyridyl or thienyl, $R^2$ particularly preferably represents $C_1$-$C_8$-alkyl, $C_2$-$C_4$-alkenyl, methoxyethyl, ethoxyethyl or represents phenyl or benzyl, $R^6$ and $R^7$ independently of one another particularly preferably represent methyl, ethyl or together represent a $C_5$-alkylene radical in which the $C_3$-methylene group is replaced by oxygen.

Very particular preference is given to using active compound/beneficial species combinations comprising compounds of the formula (I) mentioned above in which the radicals are as defined below:

W very particularly preferably represents hydrogen or methyl,

X very particularly preferably represents chlorine, bromine or methyl,

Y and Z independently of one another very particularly preferably represent hydrogen, chlorine, bromine or methyl, A, B and the carbon atom to which they are attached very particularly preferably represent saturated $C_6$-cycloalkyl in which optionally one ring member is replaced by oxygen and which is optionally monosubstituted by methyl, trifluoromethyl, methoxy, ethoxy, propoxy or butoxy, G very particularly preferably represents hydrogen (a) or represents one of the groups

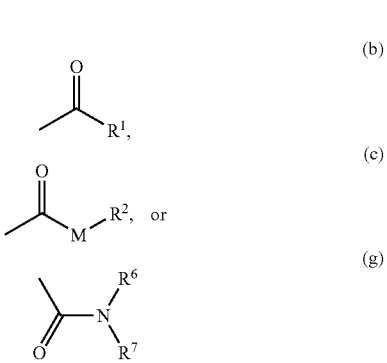

in which

M represents oxygen or sulphur, $R^1$ very particularly preferably represents $C_1$-$C_8$-alkyl, $C_2$-$C_4$-alkenyl, methoxymethyl, ethoxymethyl, ethylthiomethyl, cyclopropyl, cyclopentyl, cyclohexyl or represents phenyl which is optionally monosubstituted by fluorine, chlorine, bromine, methyl, methoxy, trifluoromethyl, trifluoromethoxy, cyano or nitro, represents in each case optionally chlorine- or methyl-substituted pyridyl or thienyl, $R^2$ very particularly preferably represents $C_1$-$C_8$-alkyl, $C_2$-$C_4$-alkenyl, methoxyethyl, ethoxyethyl, phenyl or benzyl, $R^6$ and $R^7$ independently of one another very particularly preferably represent methyl, ethyl or together represent a $C_5$-alkylene radical in which the $C_3$-methylene group is replaced by oxygen in the form of their isomer mixtures or pure isomers.

Especially preferred is the use of active compound/beneficial species combinations comprising compounds of the formula (I) mentioned above in which the radicals are as defined below:

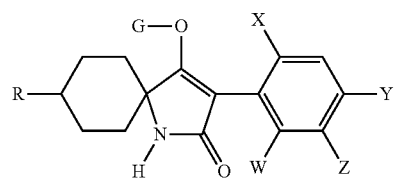

| Example No. | W | X | V | Z | R | G | m.p. ° C. |
|---|---|---|---|---|---|---|---|
| I-1 | H | Br | H | $CH_3$ | $OCH_3$ | $CO$-i-$C_3H_7$ | 122 |
| I-2 | H | Br | H | $CH_3$ | $OCH_3$ | $CO_2$—$C_2H_5$ | 140-142 |
| I-3 | H | $CH_3$ | H | $CH_3$ | $OCH_3$ | H | >220 |
| I-4 | H | $CH_3$ | H | $CH_3$ | $OCH_3$ | $CO_2$—$C_2H_5$ | 128 |
| I-5 | $CH_3$ | $CH_3$ | H | Br | $OCH_3$ | H | >220 |
| I-6 | $CH_3$ | $CH_3$ | H | Cl | $OCH_3$ | H | 219 |
| I-7 | H | Br | $CH_3$ | $CH_3$ | $OCH_3$ | $CO$-i-$C_3H_7$ | 217 |
| I-8 | H | $CH_3$ | Cl | $CH_3$ | $OCH_3$ | $CO_2C_2H_5$ | 162 |
| I-9 | $CH_3$ | $CH_3$ | $CH_3$ | $CH_3$ | $OCH_3$ | H | >220 |
| I-10 | $CH_3$ | $CH_3$ | H | Br | $OC_2H_5$ | $CO$-i-$C_3H_7$ | 212-214 |
| I-11 | H | $CH_3$ | $CH_3$ | $CH_3$ | $OC_2H_5$ | $CO$-n-$C_3H_7$ | 134 |
| I-12 | H | $CH_3$ | $CH_3$ | $CH_3$ | $OC_2H_5$ | $CO$-i-$C_3H_7$ | 108 |
| I-13 | H | $CH_3$ | $CH_3$ | $CH_3$ | $OC_2H_5$ | $CO$-c-$C_3H_5$ | 163 | in the form of their cis/trans-isomer mixtures or their pure cis-isomers.

Emphasis is given to combinations with beneficial species from the orders or sub-orders mentioned above and the cis-isomers of the formulae (I-3') and (I-4')

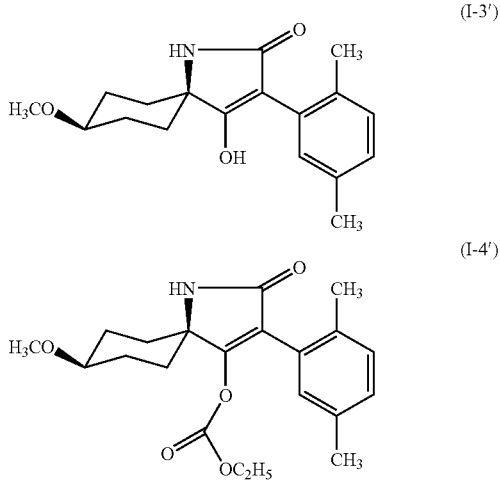

In addition, the active compound/beneficial species combinations may also comprise further suitable fungicidally, acaricidally or insecticidally active added components.

The compounds of the formula (I) are known compounds whose preparation is described in the patents/patent applications cited on page 1 (see especially WO 97/01535, WO 97/36868, WO 98/05638, WO 04/007448).

Preference is given to using beneficial species from the families of the Vespidae, Aphelinidae, Trichogrammatidae, Encyrtidae, Mymaridae, Eulophidae, Alloxystidae, Megaspilidae, Braconidae, Cantharidae, Coccinellidae, Cleridae, Chrysopidae, Hemerobiidae, Anthocoridae, Miridae, Forficulidae, Phytoseidae, Carabidae, Staphylenidae, Ichneumonidae, Aphidiidae, Eumenidae, Sphecidae, Tachnidae, Syrphidae, Cecidomyiidae, Stigmaeidae, Angstidae, Trombidiidae, Nabidae, Pentatomidae, Reduviidae, Coniopterygidae, Chameiidae, Asilidae, soil mites, in annual crops such as, for example, vegetables, melons, ornamental plants, maize, but also in perennial plants such as, for example, citrus fruit, pome fruit and stone fruit, spices, conifers and other ornamental plants, and also in afforestations.

The crops to be protected, which have only been described in a general manner, are described in a more differentiated and more specific manner below. Thus, with respect to the use, vegetable is to be understood as meaning, for example, fruit vegetables and flower-heads as vegetables, for example bell peppers, chilli peppers, tomatoes, aubergines, cucumbers, cucurbits, courgettes, broad beans, runner beans, bush beans, peas, artichokes;

but also leafy vegetables, for example lettuce, chicory, endives, cress, rocket salad, field salad, iceberg lettuce, leek, spinach, Swiss chard;

furthermore tuber vegetables, root vegetables and stem vegetables, for example celeriac, beetroot, carrots, garden radish, horseradish, scorzonera, asparagus, table beet, palm shoots, bamboo shoots, moreover bulb vegetables, for example onions, leek, fennel, garlic;

furthermore *brassica* vegetables, such as cauliflowers, broccoli, kohlrabi, red cabbage, white cabbage, green cabbage, Savoy cabbage, Brussels sprouts, Chinese cabbage.

With respect to the use, perennial crops are to be understood as meaning citrus fruit, such as, for example, oranges, grapefruit, mandarins, lemons, limes, bitter oranges, cumquats, satsumas;

but also pome fruit, such as, for example, apples, pears and quince, and stone fruit, such as, for example, peaches, nectarines, cherries, plums, common plums, apricots;

furthermore grapevine, hops, olives, tea, and tropical crops, such as, for example, mangoes, papayas, figs, pineapples, dates, bananas, durians, kakis, coconuts, cacao, coffee, avocados, lychees, maracujas, guavas, moreover almonds and nuts, such as, for example, hazelnuts, walnuts, pistachios, cashew nuts, brazil nuts, pecan nuts, butter nuts, chestnuts, hickory nuts, macadamia nuts, peanuts, additionally also soft fruit, such as, for example, blackcurrants, gooseberries, raspberries, blackberries, blueberries, strawberries, red bilberries, kiwis, cranberries.

With respect to the use, ornamental plants are to be understood as meaning annual and perennial plants, for example cut flowers, such as, for example, roses, carnations, gerbera, lilies, marguerites, chrysanthemums, tulips, daffodils, anemones, poppies, amaryllis, dahlias, azaleas, malves, but also, for example, bedding plants, potted plants and shrubs, such as, for example, roses, tagetes, pansies, geraniums, fuchsias, hibiscus, chrysanthemums, busy lizzies, cyclamen, African violets, sunflowers, begonias, furthermore, for example, bushes and conifers, such as, for example, fig trees, rhododendron, spruce trees, fir trees, pine trees, yew trees, juniper trees, stone pines, rose bays.

With respect to the use, spices are to be understood as meaning annual and perennial plants, such as, for example, aniseed, chilli pepper, bell pepper, pepper, vanilla, marjoram, thyme, cloves, juniper berries, cinnamon, tarragon, coriander, saffron, ginger.

From the family of Eumenidae, particular preference is given to: *Eumenes* spp., *Oplomerus* spp., in crops such as, for example, pome fruit, stone fruit, vegetables, ornamental plants, conifers and spices.

From the family of Sphecidae, particular preference is given to: *Ammophila sabulos, Cerceris arenaria*, in crops such as, for example, pome fruit, stone fruit, vegetables, ornamental plants, conifers and spices.

From the family of Vespidae, particular preference is given to: *Polistes* spp. *Vespa* spp., *Dolichovespula* spp., *Vespula* spp., *Paravespula* spp., in crops such as, for example, pome fruit, stone fruit, vegetables, ornamental plants, conifers and spices.

From the family of Aphelinidae, particular preference is given to: *Coccophagus* spp., *Encarsia* spp., for example, *Encarsia formosa, Aphytis* spp., *Aphelinus* spp., for example, *Aphelinus mali, Aphelinus abdominalis, Erelmocerus* spp., for example, *Erelmocerus erimicus, Erelmocerus mundus, Prospaltella* spp., in crops such as, for example, pome fruit, stone fruit, vegetables, ornamental plants, conifers and spices.

From the family of Trichogrammatidae, particular preference is given to: *Trichogramma* spp., for example, *Trichogamma brassicae*, in crops such as, for example, pome fruit, stone fruit, vegetables, ornamental plants, conifers and spices.

From the family of Encyrtidae, particular preference is given to: *Encyrtus fuscicollis, Aphidencyrtrus* spp., in crops such as, for example, pome fruit, stone fruit, vegetables, ornamental plants, conifers, spices and afforestations.

From the family of Mymaridae, in crops such as, for example, pome fruit, stone fruit, vegetables, ornamental plants, conifers and spices.

From the family of Ichneumoidae, particular preference is given to: *Coccigomymus* spp. *Diadegma* spp., *Glypta* spp., *Ophion* spp., *Pimpla* spp., in crops such as, for example, pome fruit, stone fruit, vegetables, ornamental plants, conifers and spices.

From the family of Eulophidae, particular preference is given to: *Dyglyphus* spp., for example, *Dyglyphus isaea*,

*Eulophus viridula, Colpoclypeus florus*, in crops such as, for example, pome fruit, stone fruit, vegetables, ornamental plants, conifers, maize and spices.

From the family of Alloxystidae, particular preference is given to: *Alloxysta* spp., in crops such as, for example, pome fruit, stone fruit, vegetables, ornamental plants, conifers and spices.

From the family of Megaspilidae, particular preference is given to: *Dendrocerus* spp., in crops such as, for example, pome fruit, stone fruit, vegetables, ornamental plants, conifers and spices.

From the family of Braconidae, particular preference is given to: *Aphidrus* spp., *Praon* spp., *Opius* spp., *Dacnusa* spp., for example, *Dacnusa sibiria, Apanteles* spp., *Ascogaster* spp., *Macrocentrus* spp., in crops such as, for example, pome fruit, stone fruit, vegetables, ornamental plants, conifers and spices.

From the family of Aphidiidae, particular preference is given to: *Aphidius* spp., for example, *Aphidius colemani, Aphidius ervi, Diaeretiella* spp., *Lysiphlebus* spp., in crops such as, for example, pome fruit, stone fruit, vegetables, ornamental plants, conifers and spices.

From the family of Coccinellidae, particular preference is given to: *Harmonia* spp., *Coccinella* spp., for example, *Coccinella septempunctata, Adalia* spp., for example, *Adalia bipunctata, Calvia* spp., *Chilocorus* spp., for example, *Chilocorus bipustulatus, Scymnus* spp., *Cryptolaemus montrouzieri, Exochomus* spp., *Stethorus* spp., for example, *Scymnus abietes, Scymnus interruptus, Anatis* spp., *Rhizobius* spp., *Thea* spp., in crops such as, for example, pome fruit, stone fruit, vegetables, ornamental plants, conifers and spices.

From the family of Staphylemidae, particular preference is given to: *Aleochara* spp., *Aligota* spp., *Philonthus* spp., *Staphylinus* spp., in crops such as, for example, pome fruit, stone fruit, vegetables, ornamental plants, conifers and spices.

From the family of Chrysopidae, particular preference is given to: *Chrysopa* spp., for example, *Chrysopa oculata, Chrysopa perla, Chrysopa carnea, Chrysopa flava, Chrysopa septempunctata, Chrysoperla* spp., *Chrysopidia* spp., for example, *Chrysopidia ciliata, Hypochrysa* spp., for example, *Hypochrysa elegans*, in crops such as, for example, pome fruit, stone fruit, vegetables, ornamental plants, conifers and spices.

From the family of Hemerobiidae, particular preference is given to: *Hemerobius* spp., for example, *Hemerobius fenestratus, Hemerobius humulinus, Hemerobius micans, Hemerobius nitidulus, Hemerobius pini, Wesmaelius* spp., for example, *Wesmaelius nervosus*, in crops such as, for example, pome fruit, stone fruit, vegetables, ornamental plants, conifers and spices.

From the family of Anthocoridae, particular preference is given to: *Anthocoris* spp., for example, *Anthocoris nemoralis, Anthocoris nemorum, Orius* spp., for example, *Orius majusculus, Orius minutus, Orius laevigatus, Orius insidiosus, Orius niger, Orius vicinus*, in crops such as, for example, pome fruit, stone fruit, vegetables, ornamental plants, conifers and spices.

From the family of Miridae, particular preference is given to: *Atractotomus* spp., for example, *Atractotomus mali, Blepharidopterus* spp., for example, *Blepharidopterus angulatus, Camylomma* spp., for example, *Camylomma verbasci, Deraeocoris* spp., *Macrolophus* spp., for example, *Macrolophus caliginosus*, in crops such as, for example, pome fruit, stone fruit, vegetables, ornamental plants, conifers and spices.

From the family of Pentatomidae, particular preference is given to: *Arma* spp., *Podisus* spp., for example, *Podisus maculiventris*, in crops such as, for example, pome fruit, stone fruit, vegetables, ornamental plants, conifers and spices.

From the family of Nabidae, particular preference is given to: *Nabis* spp., for example, *Nabis apterus*, in crops such as, for example, pome fruit, stone fruit, vegetables, ornamental plants, conifers and spices.

From the family of *Reduviidae*, particular preference is given to: *Macrolophus caliginosus, Empicornis vagabundus, Reduvius personatus, Rhinocoris* spp., in crops such as, for example, pome fruit, stone fruit, vegetables, ornamental plants, conifers and spices.

From the family of Tachinidae, particular preference is given to: *Bessa fugax, Cyzenius albicans, Compsileura concinnata, Elodia tragica, Exorista larvarum, Lyphia dubia*, in crops such as, for example, pome fruit, stone fruit, vegetables, ornamental plants, conifers and spices.

From the family of Syrphidae, particular preference is given to: *Dasysyrphus* spp., *Episyrphus balteatus, Melangyna triangulata, Melanostoma* spp., *Metasyrphus* spp., *Platycheirus* spp., *Syrphus* spp., in crops such as, for example, pome fruit, stone fruit, vegetables, ornamental plants, conifers and spices.

From the family of Cecidomyiidae, particular preference is given to: *Aphidoletes aphidimyza, Feltiella acarisuga*, in crops such as, for example, pome fruit, stone fruit, vegetables, ornamental plants, conifers and spices.

From the family of Phytoseidae, particular preference is given to: *Amblyseius* spp., *Thyphlodromus* spp., *Phytoseiulus* spp., in crops such as pome fruit, stone fruit, vegetables, ornamental plants and spices.

The active compound/beneficial species combinations according to the invention are suitable for controlling animal pests, preferably arthropods and nematodes, in particular insects and/or arachnids, found in viticulture and the cultivation of fruit, in agriculture and horticulture and in afforestations. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulfite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combination according to the invention can be present in commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compound combinations can be used as such, in the form of concentrates or generally customary formulations such as powders, granules, solutions, suspensions, emulsions or pastes.

The abovementioned formulation can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed by the genetic material from *Bacillus Thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plant cultivars will be developed and/or marketed in the future.

The plants listed can be treated according to the invention in a particularly advantageous manner with the active compound/beneficial species combinations according to the invention. The preferred ranges stated above for the combinations also apply to the treatment of these plants. Particular emphasis is given to the treatment of plants with the active compound/beneficial species combinations specifically mentioned in the present text.

The good insecticidal and acaricidal action of the active compound/beneficial species combinations according to the invention can be seen from the examples which follow. While the individual active compounds show weaknesses in their action, the active compound/beneficial species combinations show an action which exceeds a simple active compound action.

Formula for the Calculation of the Kill Rate of a Combination of Two Active Compounds The expected activity for a given combination of two active compounds can be calculated (cf. Colby, S. R.; "Calculating Synergistic and Antagonistic Responses of Herbicide Combinations", Weeds 15, pages 20-22, 1967) as follows:

If
X is the kill rate, expressed in % of the untreated control, when employing active compound A at an application rate of m ppm or g/ha,
Y is the kill rate, expressed in % of the untreated control, when employing active compound B at an application rate of n ppm or g/ha,
E is the kill rate, expressed in % of the untreated control, when employing active compounds A and B at application rates of m and n ppm or g/ha,
then $$E = X + Y - \frac{X \times Y}{100}$$

If the actual insecticidal kill rate is higher than the calculated one, the kill rates of the combination are superadditive, i.e. a synergistic effect is present. In this case, the kill rate that is actually observed has to be higher than the value, calculated using the formula above, for the expected kill rate (E).

USE EXAMPLES

Example A

*Bemisia tabaci* Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) infested by the whitefly (*Bemisia tabacii*) are treated by being sprayed with the preparation of active compound at the desired concentration.

After the desired period of time, a defined amount of mirid bugs (*Macrolophus caliginosus*) is added.

After the desired period of time, the kill of the pest in % is determined. 100% means that all whiteflies have been killed; 0% means that none of the whiteflies have been killed. The determined kill rates are entered into Colby's formula.

In this test, for example, the following active compound/mirid bug combination according to the present application shows a synergistically enhanced activity compared to the components applied individually:

TABLE A

| Active compound | Plant-damaging insects *Bemisia tabaci* test | | |
|---|---|---|---|
| | Concentration in ppm or number of animals | Kill in % after $14^d$ | |
| Ex. I-4' | 0.16 | 0 | |
| *Macrolophus caliginosus* | 5 | 18.2 | |
| | | found* | calc.** |
| Ex. I-4' + *Macrolophus caliginosus* | 0.16 + 5 animals | 72.7 | 18.2 |

*found = activity found
**calc. = activity calculated using Colby's formula

Example B

*Myzus persicae* Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) infested by the green peach aphid (*Myzus persicae*) are treated by being sprayed with the preparation of active compound at the desired concentration.

After the desired period of time, a defined amount of ladybird larvae (*Coccinella septempunctata*) is added.

After the desired period of time, the kill of the pest in % is determined. 100% means that all aphids have been killed; 0% means that none of the aphids have been killed.

The determined kill rates are entered into Colby's formula.

In this test, for example, the following active compound/beneficial species combination according to the present application shows a synergistically enhanced activity compared to the components applied individually:

TABLE B

| Active compound | Plant-damaging insects *Myzus persicae* test | | |
|---|---|---|---|
| | Concentration in ppm or number of animals | Kill in % after $7^d$ | |
| Ex. I-4' | 4 | 10 | |
| *Coccinella septempunctata* | 1 | 10 | |
| | | found* | calc.** |
| Ex. I-4' + *Coccinella septempunctata* | 4 + 1 animal | 70 | 19 |

*found = activity found
**calc. = activity calculated using Colby's formula

Example C

In three replications, in each case three about 25-year old apple trees (crown height about 2 m) of the cultivar "Elan" are treated against woolly apple aphids, *Eriosoma lanigerum*. Here, the active compound (I-4') (150 OD) and the commercial standard clothianidin (WG 50) are tested comparatively at the stated application rates in the presence of the woolly aphid parasite (beneficial species) *Aphelinus mali*. The application is carried out using an atomizer at a water application rate of 500 l/ha. Both one and two applications at an interval of 34 days are carried out.

Evaluation is carried out 7, 30, 44, 52, 59, 66 and 73 days after the first treatment by evaluating the kill of the adult pests and the number of parasitic pests in each case 10 colonies according to Abbott. Here, the active compound (I-4') is compared after only one treatment to the standard after two treatments, since, after two treatments, the active compound (I-4') shows an activity of 100% leaving no food (prey) for the beneficial species.

| Application rate g/ha/m | Activity (% Abbott) *Eriosoma lanigerum* | | | | | | |
|---|---|---|---|---|---|---|---|
| crown height | 7 d | 30 d | 44 d | 52 d | 59 d | 66 d | 73 d |
| Clothianidin 37.5 | 71 | 76 | 85 | 81.8 | 81.8 | 80 | 80 |
| (I-4') 75 | 48 | 95 | 99 | 99.4 | 98.2 | 98 | 98 |
| Control water | 0 | 0 | 0 | 0 | 0 | 0 | 0 |

| Application rate g/ha/m | Parasitization by beneficial species (%) *Aphelinus mali* | | | | | | |
|---|---|---|---|---|---|---|---|
| crown height | 7 d | 30 d | 44 d | 52 d | 59 d | 66 d | 73 d |
| Clothianidin 37.5 | 0 | 0 | 0 | 1 | 10 | 24 | 50 |
| (I-4') 75 | 0 | 0 | 0 | — | 35 | 54 | 90 |
| Control water | 0 | 0 | 1 | 3 | 51 | 75 | 97 |

In 4 replications, pear trees of the cultivar "Conference" of a height of about 3 m are treated against pear psyllids, *Psylla pyri*. Here, the active compound (I-4') (100 OD) and the commercial standard Amitraz (UL 400) are applied at the stated application rates. The application is carried out using a knapsack sprayer and an application rate of 1000 l of water/ha. The beneficial species *Anthocoris nemoralis* appears 14 days after the treatment.

Evaluation is carried out 4, 8 and 14 days after the treatment by evaluating the kill of the L-1 nymphs and the L-4 nymphs on the branches.

| Application rate | Activity (% Abbott) *Psylla piri* | | | | | | Number of *Anthocoris nemoralis* | | |
|---|---|---|---|---|---|---|---|---|---|
| g/ha/m | L-1 | L-4 | L-1 | L-4 | L-1 | L-4 | | | |
| crown height | 4 d | 4 d | 8 d | 8 d | 14 d | 14 d | 4 d | 8 d | 14 d |
| Amitraz 400 | 23.6 | 0.0 | 41.0 | 44.6 | 41.8 | 44.4 | | | 5 |
| (I-4') 75 | 62.7 | 91.4 | 69.5 | 98.4 | 76.6 | 99.3 | | | 12 |
| Control | | | | | | | 0 | 0 | 15 |

Example D

Critical Concentration Test/Soil Insects—Treatment of Transgenic Plants

| | |
|---|---|
| Test insect: | *Diabrotica balteata* - larvae in soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example E

*Heliothis virescens* Test—Treatment of Transgenic Plants

| | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp., USA) are treated by being dipped into the preparation of active compound of the desired concentration and are populated with the tobacco bud worm *Heliothis virescens* while the leaves are still moist.

After the desired period of time, the kill of the insects is determined.

The invention claimed is:
1. An active compound/beneficial species combination, comprising the compound of the formula (I-4):

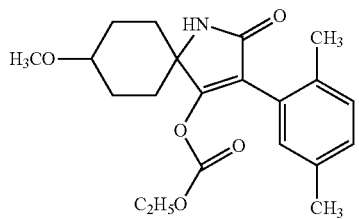
(I-4)

and one or more beneficial species selected from the group consisting Macrolophus, Coccinella, Aphelinus and Anthocoris.

2. The combination according to claim 1, comprising the compound of the formula (I-4')

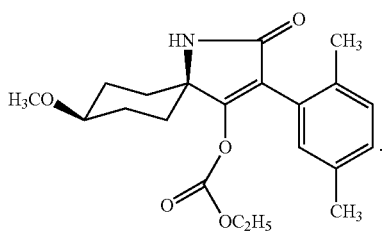
(I-4')

3. A method for controlling animal pests, comprising contacting the animal pests or their habitat with an active compound/beneficial species combination according to claim 1, wherein said animal pests are selected from the group consisting of insects, acarids, arthropods, nematodes, arachnids and mites.

4. A process for preparing an insecticidal or an acaricidal composition, comprising mixing an active compound/beneficial species combination according to claim 1 with one or more extenders, surfactants, or combinations thereof.

5. A method for reducing spray applications (number of applications per season), comprising contacting animal pests or their habitat with an active compound/beneficial species combination according to claim 1, wherein said animal pests are selected from the group consisting of insects, acarids, arthropods, nematodes, arachnids and mites.

6. A method for reducing the total insecticide or acaricide residues on harvested material and in the environment, comprising contacting animal pests or their habitat with an active compound/beneficial species combination according to claim 1, wherein said animal pests are selected from the group consisting of insects, acarids, arthropods, nematodes, arachnids and mites.

7. A composition, comprising an active compound/beneficial species combination according to claim 1 and one or more extenders, surfactants, or combinations thereof.

* * * * *